United States Patent [19]

Law

[11] Patent Number: 4,524,219
[45] Date of Patent: Jun. 18, 1985

[54] PROCESS FOR SQUARAINE COMPOSITIONS FROM HALF ESTERS OF SQUARIC ACID

[75] Inventor: Kock-Yee Law, Fairport, N.Y.

[73] Assignee: Xerox Corporation, Stamford, Conn.

[21] Appl. No.: 576,656

[22] Filed: Feb. 3, 1984

[51] Int. Cl.$^3$ ............... C07C 85/00; C07C 85/02; C07C 85/06
[52] U.S. Cl. ........................................... 564/307
[58] Field of Search ............................... 564/307

[56] References Cited

U.S. PATENT DOCUMENTS

| | | | |
|---|---|---|---|
| 2,957,918 | 10/1960 | Smutny et al. | 260/590 |
| 3,617,270 | 11/1971 | Kampfer | 96/1.7 |
| 4,028,418 | 6/1977 | Van den Brink et al. | 260/586 C |
| 4,159,387 | 6/1979 | Bellus | 560/185 |
| 4,216,172 | 8/1980 | Heine et al. | 568/364 |

OTHER PUBLICATIONS

White et al., "J.A.C.S.", 86, pp. 453–458, 2164.
The Chemistry of Squaraines, Schmidt, Oxocarbon, (1980), pp. 185–231.

Primary Examiner—Paul F. Shaver
Attorney, Agent, or Firm—E. O. Palazzo

[57] ABSTRACT

This invention relates to an improved process for the preparation of squaraine compositions which comprises reacting an alkyl squarate, with an aniline, in the presence of an optional acid catalyst and an aliphatic alcohol.

18 Claims, No Drawings

PROCESS FOR SQUARAINE COMPOSITIONS FROM HALF ESTERS OF SQUARIC ACID

BACKGROUND OF THE INVENTION

This invention generally relates to an improved process for preparing squaraine compositions, and more specifically, the present invention is directed to an improved process for the preparation of squaraine compositions from the half esters of squaric acid. In one embodiment, the present invention involves the preparation of certain squaraine compositions by the reaction of an alkyl squarate with aniline derivatives. The squaraine compositions resulting from this process are useful for incorporation into layered photoresponsive imaging devices wherein, for example, the sensitivity thereof can be varied or enhanced, enabling these devices to be capable of being responsive to visible light, and infrared illumination needed for laser printing, especially with gallium arsenide diode lasers. Accordingly, there is envisioned photoresponsive devices containing the squaraine compositions prepared in accordance with the present invention, situated between a photogenerating layer and a hole transport layer, or situated between a photogenerating layer and a supporting substrate of the device.

Photoconductive imaging members containing certain squaraine compositions, particularly hydroxy squaraines, are known. Also known are layered photoresponsive devices with photogenerating layers and transport layers, reference U.S. Pat. No. 4,265,990. Examples of photogenerating layers disclosed in this patent include trigonal selenium, and phthalocyanines, while examples of transport layers that may be selected are comprised of certain diamine dispersed in an inactive resinous binder composition. Moreover, the use of certain squaraine pigments in photoresponsive imaging devices is disclosed in a copending application, wherein there is described an improved photoresponsive device containing a substrate, a hole blocking layer, an optional adhesive interface layer, an inorganic photogenerating layer, a photoconductive composition capable of enhancing or reducing the intrinsic properties of the photogenerating layer, and a hole transport layer. As photoconductive compositions for this device, there can be selected various squaraine pigments, including hydroxy squaraine compositions of the formula as outlined on page 13, beginning at line 21 of the copending application, U.S. Ser. No. 414,997, the disclosure of which is totally incorporated herein by reference, entitled Multilayered Photoresponsive Device for Electrophotography. Additionally, there is disclosed in U.S. Pat. No. 3,824,099 certain photosensitive hydroxy squaraine compositions. According to the disclosure of this patent, the squaraine compositions are photosensitive in normal electrostatographic imaging systems.

In another copending application, there is described novel squaraine compositions of matter, such as bis-9-(8-hydroxyjulolidinyl)squaraine, and the use of these compositions as imaging members. One of the imaging members disclosed contains a supporting substrate, a hole blocking layer, an optional adhesive interface layer, an inorganic photogenerating layer, a photoconducting composition layer capable of enhancing or reducing the intrinsic properties of the photogenerating layer, which compositions are comprised of the novel julolidinyl squaraines materials illustrated in the copending application, and a hole transport layer.

Processes for preparing squaraine compositions generally involve the reaction of squaric acid with an amine. Thus, for example, the novel julolidinyl squaraine compositions disclosed in the referenced copending application are prepared by the reaction of an aromatic amine and squaric acid, in a molar ratio of from about 1.5:1 to 3:1 in the presence of a mixture of an aliphatic alcohol and an optional azeotropic cosolvent. About 200 milliliters of alcohol per 0.1 mole of squaric acid are used, while from about 40 milliliters to about 4,000 milliliters of azeotropic material are selected. The squaric acid reaction is generally accomplished at a temperature of from about 50 degrees Centigrade to about 130 degrees Centigrade. Illustrative examples of amine reactants include 8-hydroxyjulolidine, while examples of aliphatic alcohol selected include 1-butanol, with the azeotropic materials being aromatic compositions such as benzene and toluene. Moreover, there is disclosed in a copending application, U.S. Ser. No. 557,796/83, entitled Synthesis of Photoconductive Squaraines, the disclosure of which is totally incorporated herein by reference, processes for preparing squaraine compositions by the reaction of a dialkyl squarate and an aromatic aniline. More specifically, there is disclosed in this copending application an improved process for the preparation of squaraine compositions which comprises reacting a dialkyl squarate, with an aniline, in the presence of an acid catalyst and an aliphatic alcohol, at a temperature of from about 60 degrees Centigrade to about 160 degrees Centigrade.

While the above processes for preparing squaraine compositions may be suitable for their intended purposes, there continues to be a need for other processes wherein squaraine compositions, useful as photoconductive materials, can be prepared. Additionally, there remains a need for simple, economical processes for preparing squaraine compositions wherein the squaraine products obtained contain substantially less impurities than those squaraines resulting from the squaric acid process, as it is believed that the presence of impurities in the squaraine compositions resulting from the squaric acid process causes the photosensitivity of these compositions to vary significantly, and in many instances, to be lower than the squaraine compositions prepared in accordance with the process of the present invention. Further, there continues to be a need for novel squaraine compositions which, when selected for layered photoresponsive imaging devices, allow the generation of acceptable images, and wherein such devices can be repeatedly used in a number of imaging cycles without deterioration thereof from the machine environment or surrounding conditions. Moreover, there remains a need for processes for preparing certain squaraine compositions, wherein the resulting products when incorporated into imaging members exhibit excellent dark decay and superior photosensitivity. Also, there is provided in accordance with the process of the present invention xerographic photoconductive devices comprised of the infrared sensitive squaraine photogenerating materials prepared in accordance with the process of the present invention and possessing desirable sensitivity, low dark decay, and high charge acceptance values.

SUMMARY OF THE INVENTION

It is therefore an object of the present invention to provide improved processes for preparing squaraine compositions.

In another object of the present invention, there are provided improved processes for preparing certain squaraine compositions, with enhanced photosensitivity, excellent dark decay properties, and acceptable charge acceptance.

In yet another object of the present invention, there are provided simple, economical processes for preparing certain squaraine compositions.

In still a further object of the present invention, there are provided improved processes for obtaining squaraine compositions of matter, which contain substantially less impurities than similar squaraines prepared by the known squaric acid process.

In another object of the present invention, there are provided improved processes for obtaining hydroxy squaraines, julolidine squaraines, fluorinated squaraines and other squaraines, by the reaction of an alkyl squarate with an aromatic aniline.

A further object of the present invention resides in the preparation of squaraine compositions wherein the particle sizes of the resulting products are desirably less than about two microns or about a factor of two smaller in many instances than those squaraine materials prepared from the known squaric acid process.

These and other objects of the present invention are generally accomplished by the reaction of an alkyl squarate, and an aniline, in the presence of an aliphatic alcohol. More specifically, the process of the present invention comprises reacting at an effective temperture, for example, from about 60 degrees Centigrade to about 160 degrees Centigrade, an alkyl squarate, with a dialkyl aniline, in the presence of an optional acid catalyst, and an aliphatic alcohol. The reactions involved are represented by the following illustrative equations:

I. General Reaction

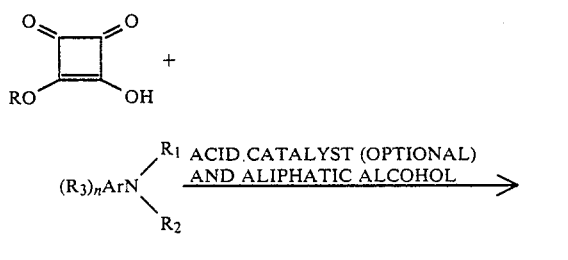

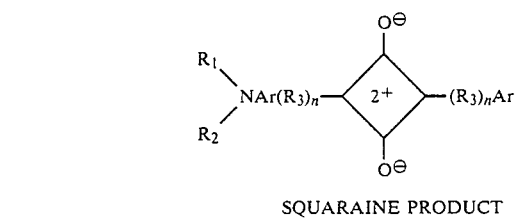

SQUARAINE PRODUCT

II. Specific Reaction

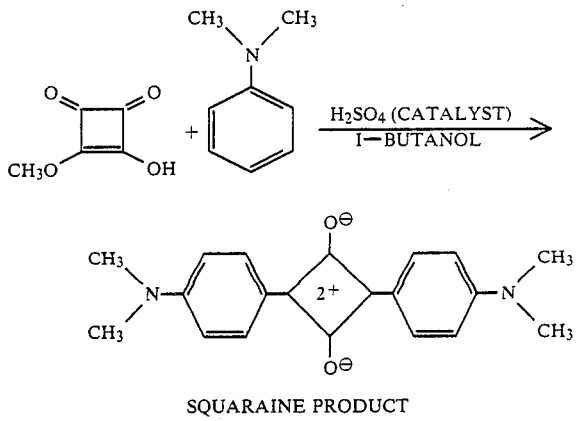

SQUARAINE PRODUCT wherein R, $R_1$, and $R_2$ are independently selected from alkyl groups, $R_3$ is an alkyl group, a hydroxy group, hydrogen, or fluorine, Ar is an aromatic group, and n is the number zero or 1.

Alkyl substituents include those containing of from about 1 carbon atom to about 10 carbon atoms, and preferably from 1 carbon atom to about 6 carbon atoms, such as methyl, ethyl, propyl, butyl, pentyl, hexyl, and the like. Preferred alkyl groups are methyl, ethyl, propyl, and butyl.

Aromatic substituents include those containing from about 6 carbon atoms to about 24 carbon atoms such as phenyl, and naphthal, with phenyl being preferred.

The $R_3$ substituents, as indicated, can be an alkyl group, as defined herein, or may be selected from hydroxy, hydrogen, or fluorine.

Illustrative examples of alkyl squarate reactants include methyl squarate, propyl squarate, ethyl squarate, butyl squarate, pentyl squarate, hexyl squarate, heptyl squarate, octyl squarate, and the like, with the methyl, ethyl, propyl, and butyl squarates being preferred. Illustrative examples of aniline reactants include N,N-dimethylaniline, N,N-diethylaniline, N,N-dipropylaniline, N,N-dibutylaniline, N,N-dipentylaniline, N,N-dihexylaniline, 3-methyl-N,N-dimethylanilne, 3-hydroxy-N,N-dimethylaniline, 3-fluoro-N,N-dimethylaniline, 3-hydroxy-N,N-diethylaniline, 3-ethyl-N,N-dimethylaniline and the like.

The reaction is preferably accomplished in the presence of an optional acid catalyst, examples of which include various inorganic acids, and organic acids, such as sulfuric acid, trichloroacetic acid, oxalic acid, toluene sulfonic acid, and the like, with sulfuric acid and trichloroacetic acid being preferred.

Known solvents, such as aliphatic alcohols, including methanol, ethanol, propanol, butanol, amyl alcohol, and the like are selected for the purpose of forming a solution of the squarate and the acid catalyst. Other solvents can be used providing the objectives of the present invention are accomplished.

The reaction temperature can vary over a wide range, and is generally dependent on the reactants selected, and other similar factors. Generally, the reaction temperature is established at a temperature at which the aliphatic alcohol boils. Thus, for example, the reaction temperature is generally from about 60 degrees Centigrade to about 160 degrees Centigrade, and is preferably from about 98 degrees Centigrade to about 140 degrees Centigrade, especially when the aliphatic alcohol selected contains a carbon chain length of from about 3 carbon atoms to about 5 carbon atoms.

The amount of reactants and catalyst selected depend on a number of factors, including the specific reactants used, and the reaction temperature involved. Generally, however, from about 5 millimoles, to about 50 millimoles, of alkyl squarate, with about 10 millimoles to about 100 millimoles of aniline, and from about 5 milliliters to about 200 milliliters of aliphatic alcohol are selected. Also from about 1 millimole to about 40 millimoles of protons, are contained in the optional acid catalyst.

The resulting products subsequent to separation from the reaction mixture, by known techniques, including filtration, were identified primarily by melting point data, infrared analysis, and visible absorption spectroscopy. Additionally, the data generated from these techniques was compared with similar data available for the identical compounds prepared from the squaric acid process.

Illustrative examples of specific squaraine compositions resulting from the process of the present invention include bis(4-dimethylaminophenyl)squaraine, bis(4-diethylaminophenyl)squaraine, bis(2-fluoro-4-dimethylaminophenyl)squaraine, bis(2-hydroxy-4-dimethylaminophenyl)squaraine, bis(2-hydroxy-4-diethylaminophenyl)squaraine, bis(2-methyl-4-dimethylaminophenyl)squaraine, and the like. The fluorinated squaraine compositions prepared in accordance with the process of the present invention are believed to be novel compositions of matter. These compositions are described in copending application U.S. Ser. No. 558,224/83, entitled Photoconductive Devices Containing Novel Squaraine Compositions, the disclosure of which is totally incorporated herein by reference.

In one specific embodiment, the process of the present invention comprises forming a solution of the alkyl squarate reactant, and acid catalyst, by mixing together from about 5 to about 50 millimoles of an alkyl squarate, from about 10 to about 100 millimoles of an aromatic aniline, with from about 0.05 milliliters to about 1 milliliter of sulfuric acid, and from about 5 milliliters to about 200 milliliters of aliphatic alcohol. This mixture is then heated to a temperature of from about 60 degrees Centigrade to about 160 degrees Centigrade, with continual stirring. After heating, for a period of about 24 hours, the reaction mixture is allowed to cool and there is isolated by filtration the desired squaraine product. The products obtained were of a small particle size, ranging from about less than 0.1 microns to about less than 2.0 microns, which small particle sizes provide for the superior dispersion of these squaraine compositions in a resinous binder composition, thereby enabling excellent dark decay properties, high charge acceptance and superior photosensitivity for photoconductive members thereof, as compared to devices containing similar squaraines prepared by the squaric acid process.

The squaraine compositions prepared in accordance with the process of the present invention, including the novel fluorinated squarines are useful as photoconductive substances. Thus there can be prepared a layered photoresponsive device comprised of a supporting substrate, a hole transport layer, and a photoconductive layer, comprised of the squaraine compositions prepared in accordance with the process of the present invention, which composition is situated between the supporting substrate and a hole transport layer. In another embodiment, the photoresponsive device envisioned is comprised of a substrate, a photoconducting layer, comprised of the squaraine compositions prepared in accordance with the process of the present invention, and situated between the photoconducting squaraine layer, and the supporting substrate, a hole transport layer. Additionally, there can be prepared photoresponsive devices useful in printing systems wherein the imaging member is comprised of a layer of the squaraine photoconductive composition prepared in accordance with the process of the present invention, situated between a photogenerating layer, and a hole transport layer, or wherein the squaraine photoconductive squaraine composition layer is situated between a photogenerating layer, and the supporting substrate of such a device. In the latter devices, the photoconductive layer comprised of the squaraine compositions serves to enhance or reduce the intrinsic properties of the photogenerating layer in the infrared and/or visible range of the spectrum. These devices are described in a copending application U.S. Ser. No. 493,114, entitled Photoconductive Devices Containing Novel Squaraine Compositions, the disclosure of which is totally incorporated herein by reference.

One specific improved photoresponsive device containing therein the squaraines prepared in accordance with the process of the present invention is comprised in the order stated of (1) a supporting substrate, (2) a hole blocking layer, (3) an optional adhesive interface layer, (4) an inorganic photogenerator layer, (5) a photoconductive composition layer comprised of the squaraine materials prepared in accordance with the process of the present invention, and (6) a hole transport layer.

The photoresponsive devices described can be prepared by a number of known methods, reference for example the copending applications indicated, the process parameters and the order of coating of the layers being dependent on the device desired. Thus, for example, a three layered photoresponsive device can be prepared by vacuum sublimation of the photoconducting layer on a supporting substrate, and subsequently depositing by coating a solution of the hole transport layer. In another process variant, the layered photoresponsive device can be prepared by providing the conductive substrate containing a hole blocking layer and an optional adhesive layer, and applying thereto by solvent coating processes, laminating processes, or other methods, a photogenerating layer, a photoconductive composition comprised of the squaraines prepared in accordance with the process of the present invention and a hole transport layer.

The improved photoresponsive devices of the present invention can be incorporated into various imaging systems, such as those conventionally known as xerographic imaging processes. Additionally, the improved photoresponsive devices of the present invention containing an inorganic photogenerating layer, and a photoconductive layer comprised of the squaraines prepared in accordance with the process of the present invention can function simultaneously in imaging and printing systems with visible light and/or infrared light. In this embodiment, the improved photoresponsive devices of the present invention may be negatively charged, exposed to light in a wavelength of from about 400 to about 1,000 nanometers, either sequentially or simultaneously, followed by developing the resulting image and transferring to paper. The above sequence may be repeated many times.

The invention will now be described in detail with reference to specific preferred embodiments thereof, it being understood that these examples are intended to be illustrative only. The invention is not intended to be limited to the materials, conditions, or process parameters recited herein, it being noted that all parts and percentages are by weight unless otherwise indicated.

EXAMPLE I

Methyl squarate 0.64 grams, 5 millimoles, prepared as described in the *Journal American Chemical Society*, Vol. 88, pp. 1533–1536 (1966) was placed in a 100 milliliter 3-neck flask containing 0.1 milliliters of concentrated sulfuric acid, 1.23 grams, 10.2 millimoles of N,N-dimethylaniline, and 10 milliliters of dry 1-butanol (dried over 3 Angstrom molecular sieves). The above mixture was brought to reflux at an oil bath temperature of about 126° C. under a nitrogen atmosphere. After 24 hours, the mixture was cooled to room temperature, and 2 milliliters triethylanime, 30 milliliters ether/methanol (1:1) were added to the solution mixture. The precipitated product, bis(4-dimethylaminophenyl)-squaraine was separated by filtration with a medium sintered glass funnel, followed by washing with an ether/methanol (1:1) solution, this washing continuing until the filtrate is light blue. After vacuum drying, there resulted 0.59 grams (37 percent), of bis(4-dimethylaminophenyl)squaraine as identified by a comparison of its properties, including melting point, and infrared (IR) spectrum with identical data generated for the squaraine obtained from the reaction of N,N-dimethylaniline and squaric acid.

EXAMPLE II

The process of Example I was repeated with the exception that there was selected 20 milliliters of dry 1-butanol, in place of the 10 milliliters of 1-butanol, and there resulted in 47 percent yield the product bis(4-dimethylaminophenyl)squaraine. This composition was identified in accordance with the procedure of Example I, and substantially identical results were obtained.

EXAMPLE III

The process of Example I was repeated with the exception that there was selected 0.05 milliliters of concentrated sulfuric acid, in place of the 0.1 milliliters of this acid, and there resulted the product bis(4-dimethylaminophenyl)squaraine in 45 percent yield. This product was identified in accordance with the procedure of Example I, and substantially identical results were obtained.

EXAMPLE IV

The process of Example I was repeated with the exception that the optional acid catalyst sulfuric acid was eliminated and there resulted the product bis(4-dimethylaminophenyl)squaraine in 39 percent yield. This product was identified by repeating the procedure of Example I, and substantially identical results were obtained.

EXAMPLE V

The procedure of Example I was repeated with the exception that 0.05 milliliters of concentrated sulfuric acid catalyst was selected in place of 0.1 milliliters of this acid, and 20 milliliters of dry 1-butanol was used in place of 10 milliliters of dry 1-butanol, and there resulted in 47 percent yield, the product bis(4-dimethylaminophenyl)squaraine. This product was identified in accordance with the procedure of Example I, and substantially identical results were obtained.

EXAMPLE VI

Methyl squaraine 0.64 grams, 5 millimoles, was reacted with N,N-dimethylaniline, 1.23 grams, 10.2 millimoles, in a mixture of benzene 40 milliliters, and 1-butanol, 40 milliliters with reflux at an oil bath temperature of about 120° C. Water was removed azeotropically and was collected by a Dean Stark trap. After 24 hours, the mixture was cooled to room temperature. The precipitated product was separated by filtration with a medium sintered glass funnel, followed by washing with ether/methanol (1:1) solution, this washing continuing until the filtrate is light blue. This afforded bis(4-dimethylaminophenyl)squaraine, 0.65 grams, 40 percent yield, identified in accordance with the procedure of Example I.

EXAMPLE VII

Methyl squarate 0.64 grams, 5 millimoles, was placed in a 100 milliliter 3-neck flask containing 0.05 milliliters of concentrated sulfuric acid, 1.40 grams, 10.1 millimoles, m-fluoro-N,N-dimethylaniline and 20 milliliters dry 1-butanol. The above mixture was brought to reflux at an oil bath temperature of about 126° C. under a nitrogen ($N_2$) atmosphere. After about 24 hours, the mixture was cooled to room temperature and 1 milliliter of triethylanime, and 30 milliliters of an ether/methanol (1:1) solution was added. The precipitated product was isolated by filtration with a fine sintered glass funnel, followed by washing with an ether/methanol (1:1) solution, this washing continuing until the filtrate is light blue. After vacuum drying there resulted 0.17 grams (10 percent), bis(2-fluoro-4-dimethylaminophenyl)-squaraine identified by comparing the properties, melting point, and IR spectrum with the melting point and IR spectrum of the squaraine prepared from squaric acid and m-fluoro-N,N-dimethylaniline.

EXAMPLE VIII

Methyl squarate 0.64 grams, 5 millimoles, was placed in a 100 milliliter 3-neck flask containing 0.1 milliliters of concentrated sulfuric acid, 1.37 grams, 10.1 millimoles m-methyl-N,N-dimethylaniline and 20 milliliters of dry 1-butanol. The above mixture was brought to reflux at an oil bath temperature of about 126° C. under a $N_2$ atmosphere. After about 24 hours, the mixture was cooled, and 1 milliliter triethylanime, 30 milliliter ether/methanol (1:1) solution was added. The precipitated product was isolated by filtration with a medium sintered glass funnel, followed by washing with an ether/methanol (1:1) solution, this washing continuing until the filtrate is light blue. After vacuum drying there resulted 0.8 grams (46 percent), bis(2-methyl-4-dimethylaminophenyl)squaraine, identified in accordance with the procedure of Example VII wherein the comparison was accomplished with a squaraine prepared from the squaric acid and 3-methyl-N,N-dimethylaniline.

EXAMPLE IX

Methyl squarate 0.64 grams, 5 millimoles, was placed in a 100 milliliter 3-neck flask containing 0.1 milliliters of concentrated sulfuric acid, 1.39 grams, 10.1 millimoles 3-hydroxy-N,N-dimethylaniline, and 20 milliliters of dry 1-butanol. The above mixture was brought to reflux at an oil bath temperature of about 126° C. under a $N_2$ atmosphere. After about 24 hours, the mixture was cooled, and 1 milliliter of triethylanime and 30 milliliters of an ether/methanol (1:1) solution was added. The precipitated product was isolated by filtration with a fine sintered glass funnel, followed by washing with an ether/methanol (1:1) solution, this washing continued until the filtrate is light blue. After vacuum drying there resulted 1.45 grams, 82.4 percent bis(2-hydroxy-4-dimethylaminophenyl)squaraine. The product was identified by repeating the procedure of Example VIII wherein the comparison was accomplished with the squaraine prepared from squaric acid and 3-hydroxy-N,N-dimethylaniline.

Although the invention has been described with reference to specific preferred embodiments, it is not intended to be limited thereto, rather those skilled in the art will recognize that variations and modifications may be made therein which are within the spirit of the present invention and within the scope of the following claims.

I claim:

1. An improved process for the preparation of squaraine compositions which comprises reacting an alkyl squarate, with an aniline, in the presence of an aliphatic alcohol and an optional acid catalyst.

2. A process in accordance with claim 1 wherein the reaction is accomplished at a temperature of from about 60 degrees Centigrade to about 160 degrees Centigrade.

3. A process in accordance with claim 1 wherein there is further included in the reaction an acid catalyst.

4. A process in accordance with claim 1 wherein the alkyl squarate is selected from the group consisting of a methyl squarate, ethyl squarate, propyl squarate, butyl squarate, pentyl squarate, hexyl squarate or heptyl squarate.

5. A process in accordance with claim 1 wherein the aniline is selected from the group consisting of a N,N-dimethyaniline, N,N-diethylaniline, N,N-dipropylaniline, N,N-dibutylaniline, N,N-dipentylaniline, 3-fluoro-N,N-dimethylaniline, 3-hydroxy-N,N-dimethylaniline, 3-methyl-N,N-dimethylaniline, and 3-hydroxy-N,N-diethylaniline.

6. A process in accordance with claim 1 wherein the aliphatic alcohol is 1-butanol, 1-propanol, or amyl alcohol.

7. A process in accordance with claim 1 wherein the resulting squaraine product is bis(2-fluoro-4-dimethylaminophenyl)squaraine.

8. A process in accordance with claim 1 wherein the resulting squaraine product is bis(4-dimethylaminophenyl)squaraine.

9. A process in accordance with claim 1 wherein the resulting squaraine product is bis(2-hydroxy-4-dimethylaminophenyl)squaraine.

10. A process in accordance with claim 1 wherein the resulting squaraine product is bis(2-methyl-4-dimethylaminophenyl)squaraine, or bis(2-hydroxy-4-diethylaminophenyl)squaraine.

11. A process in accordance with claim 1 wherein the alkyl squarate is methyl squarate.

12. A process in accordance with claim 2 wherein there is selected from about 5 millimoles to about 50 millimoles of the alkyl squarate, from about 0.05 milliliter to about 1 milliliter of sulfuric acid, from about 10 millimoles to about 100 millimoles of aniline, and from about 5 milliliters to about 200 milliliters of aliphatic alcohol.

13. A process in accordance with claim 2 wherein the reaction temperature is from about 98 degrees Centigrade to about 140 degrees Centigrade.

14. A process in accordance with claim 2 wherein the acid catalyst is sulfuric acid, trichloroacetic acid, or oxalic acid.

15. A process for the preparation of squaraine compositions which comprises reacting in the presence of an optional acid catalyst and an aliphatic alcohol an alkyl squarate of the following formula with an aniline of the following formula:

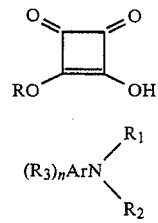

I

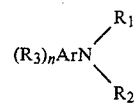

II wherein R, $R_1$, $R_2$, are independently selected from alkyl groups, and $R_3$ is an alkyl group, a hydroxy group, hydrogen, or fluorine, Ar is an aromatic group, and n is the number zero or one.

16. A process in accordance with claim 15, wherein R, $R_1$, $R_2$, and $R_3$, are alkyl groups containing from about one carbon atom to about ten carbon atoms.

17. A process in accordance with claim 15, wherein R is methyl, Ar is phenyl, $R_1$ is methyl, $R_2$ is methyl, and n is zero.

18. A process in accordance with claim 15, wherein the reaction is accomplished at a temperature of from about 60 degrees Centigrade to about 160 degrees Centigrade.

* * * * *